(12) United States Patent
Annis et al.

(10) Patent No.: US 8,303,821 B2
(45) Date of Patent: Nov. 6, 2012

(54) REDUCTION OF ANTIMICROBIAL COMPOUND LEVELS DURING PRODUCT DISPENSING

(75) Inventors: Ioana Annis, Mundelein, IL (US); Perrine Brel, Saint Laurent du Var (FR); Jean Ferraro, Buc (FR); Thierry Lacour, Le Rouret (FR); Richard Levy, Valbonne (FR); Yves Louis Walter C. Vandenberghe, Le Rouret (FR)

(73) Assignee: Rohm and Haas Company, Philadelphia, PA (US)

( * ) Notice: Subject to any disclaimer, the term of this patent is extended or adjusted under 35 U.S.C. 154(b) by 456 days.

(21) Appl. No.: 12/763,692

(22) Filed: Apr. 20, 2010

(65) Prior Publication Data
US 2010/0270241 A1 Oct. 28, 2010

(30) Foreign Application Priority Data

Apr. 23, 2009 (EP) .................................. 09290301
Mar. 19, 2010 (EP) .................................. 10290144

(51) Int. Cl.
*B01D 15/04* (2006.01)
(52) U.S. Cl. ........................................................ 210/692
(58) Field of Classification Search .................. 210/692
See application file for complete search history.

(56) References Cited

U.S. PATENT DOCUMENTS

| | | | |
|---|---|---|---|
| 3,853,758 A | 12/1974 | Hurwitz et al. | |
| 3,975,155 A | 8/1976 | Geyer | |
| 3,994,719 A | 11/1976 | Corte et al. | |
| 4,501,628 A | 2/1985 | McGuire et al. | |
| 5,135,656 A | 8/1992 | Means et al. | |
| 5,252,223 A * | 10/1993 | Goodman et al. | 210/688 |
| 5,641,411 A * | 6/1997 | Williams et al. | 210/749 |
| 5,855,899 A | 1/1999 | Batts et al. | |
| 5,922,206 A | 7/1999 | Darlington, Jr. et al. | |
| 6,464,887 B1 | 10/2002 | de la Bruniere | |
| 6,646,059 B2 | 11/2003 | Nguyen et al. | |
| 6,649,065 B2 * | 11/2003 | Boyce | 210/652 |
| 6,776,904 B2 | 8/2004 | Zhu et al. | |
| 2002/0120071 A1 | 8/2002 | Nguyen et al. | |
| 2010/0160454 A1 * | 6/2010 | McCaulley et al. | 514/729 |

FOREIGN PATENT DOCUMENTS

| | | |
|---|---|---|
| EP | 490564 | 6/1992 |
| EP | 733304 | 9/1996 |

* cited by examiner

*Primary Examiner* — Chester Barry
(74) *Attorney, Agent, or Firm* — Kenneth Crimaldi

(57) ABSTRACT

A method for reducing antimicrobial compound levels in a liquid composition containing at least one antimicrobial compound. The method comprises contacting said liquid composition with a functionalized resin. Antimicrobial compounds that may be removed by this method include isothiazolin-3-ones, e.g., 2-methyl-4-isothiazolin-3-one; 5-chloro-2-methyl-4-isothiazolin-3-one; 2-n-octyl-4-isothiazolin-3-one; 4,5-dichloro-2-n-octyl-4-isothiazolin-3-one; 1,2-benzisothiazolin-3-one and N-alkyl derivatives thereof, especially N-methyl and N-n-butyl; 2,2-dibromo-3-nitrilopropionamide (DBNPA); 2-bromo-2-nitropropanediol (BNPD); dithio-2,2'-bis(benzmethylamide) (DTBMA); hexetidine; chlorphenesin, $C_1$-$C_4$ alkyl-4-hydroxybenzoates (alkyl parabens); 3-iodopropynylbutylcarbamate (IPBC); formaldehyde releasers and mixtures thereof.

13 Claims, No Drawings

REDUCTION OF ANTIMICROBIAL COMPOUND LEVELS DURING PRODUCT DISPENSING

This patent application claims the benefit of the earlier filed European Patent Applications serial number 092903012 filed on Apr. 23, 2009 and serial number 10290144.4 filed Mar. 19, 2010 under 37 CFR 1.55(a).

This invention relates to a method for removal of isothiazolin-3-ones and other antimicrobial compounds from products during dispensing to minimize user contact with isothiazlin-3-ones and other antimicrobial compounds used to prevent antimicrobial growth in the product.

A variety of antimicrobial compounds is used to control growth of microorganisms in products. In some cases, chlorinated isothiazolin-3-ones are used to provide control of microorganisms in a particular end use environment. However, chlorinated isothiazolone-3-ones can act as sensitizers and are sometimes regarded as undesirable components in products, especially personal care products intended for direct skin contact. A method for reducing the level of isothiazolin-3-ones and other potentially irritating antimicrobial compounds during dispensing to minimize skin contact with these compounds would be desirable.

Methods are known for degrading isothiazolin-3-ones. For example, U.S. Pat. No. 5,641,411 discloses a method for detoxifying industrial effluents containing isothiazolin-3-ones by contacting the effluents with a water soluble organic thiol compound. However, there is a need for a method for treating products in situ to reduce levels of isothiazolin-3-ones without introducing other objectionable compounds into the product. The problem addressed by this invention is to provide such a method for in situ reduction of antimicrobial compounds.

STATEMENT OF THE INVENTION

The present invention is directed to a method for reducing levels of antimicrobial compounds in a liquid composition containing at least one antimicrobial compound selected from isothiazolin-3-ones, 2,2-dibromo-3-nitrilopropionamide (DBNPA), 2-bromo-2-nitropropanediol (BNPD), dithio-2,2'-bis(benzmethylamide) (DTBMA), hexetidine, chlorphenesin and $C_1$-$C_4$ alkyl-4-hydroxybenzoates (alkyl parabens). The method comprises contacting said liquid composition with a cross-linked resin comprising thiol, thiourea or thioamide functional groups.

The present invention is further directed to a method for reducing levels of 3-iodopropynylbutylcarbamate (IPBC) in a liquid composition. The method comprises contacting said liquid composition with a cross-linked resin comprising thiol, thiourea, thioamide or amino functional groups.

The present invention is further directed to a method for reducing levels of formaldehyde or formaldehyde-releasing compounds in a liquid composition. The method comprises contacting said liquid composition with a cross-linked resin comprising thiol, thiourea, thioamide or amino functional groups.

DETAILED DESCRIPTION OF THE INVENTION

Unless otherwise specified, temperatures are in degrees centigrade (° C.), references to percentages are by weight (wt %) and references to "ppm" are in parts per million by weight (weight/weight) of active ingredient (antimicrobial compound). Examples were performed at a temperature from 20° C. to 25° C., unless otherwise specified. Weights and functionality of resin are on a dry basis, unless otherwise specified. Viscosities mentioned herein are those measured using a Brookfield viscometer operating at a temperature of approximately 25° C. using spindles appropriate for the viscosity ranges measured. "MIT" is 2-methyl-4-isothiazolin-3-one, also referred to by the name 2-methyl-3-isothiazolone. "CMIT" is 5-chloro-2-methyl-4-isothiazolin-3-one. "OIT" is 2-n-octyl-4-isothiazolin-3-one. "DCOIT" is 4,5-dichloro-2-n-octyl-4-isothiazolin-3-one. "BIT" is 1,2-benzisothiazolin-3-one. A liquid composition is one which comprises a continuous liquid phase at 25° C. The liquid phase may be aqueous, an oil-in-water emulsion, or oil-based, preferably aqueous. The composition may also contain insoluble solids, which may be dispersed, suspended or emulsified. Formaldehyde releasing compounds are compounds which produce free formaldehyde in aqueous solution. Examples of formaldehyde-releasing compounds include 1-(3-chloroallyl)-3,5,7-triaza-azoniaadamantane (CTAC), 1,3-bis(hydroxymethyl)-5,5-dimethyl-2,4-dioxoimidazolidine (DMDMH), 1,3-bis(hydroxymethyl)-1-(1,3,4-tris(hydroxymethyl)-2,5-dioxoimidazolidin-4-yl)urea (diazolidinyl urea), 1,1'-methylenebis{3-[1-(hydroxymethyl)-2,5-dioxoimidazolidin-4-yl]urea (imidazolidinyl urea), sodium hydroxymethylglycinate, 4,4-dimethyloxazolidine and 7-ethylbicyclooxazolidine. Especially preferred formaldehyde-releasing compounds include 1-(3-chloroallyl)-3,5,7-triaza-azoniaadamantane and 1,3-bis(hydroxymethyl)-5,5-dimethyl-2,4-dioxoimidazolidine.

As used herein, the following terms have the designated definitions, unless the context clearly indicates otherwise. The term "antimicrobial compound" refers to a compound capable of inhibiting the growth of or controlling the growth of microorganisms at a locus; antimicrobial compounds include bactericides, bacteristats, fungicides, fungistats, algaecides and algistats, depending on the dose level applied, system conditions and the level of microbial control desired. The term "microorganism" includes, for example, fungi (such as yeast and mold), bacteria and algae.

As used herein the term "(meth)acrylic" refers to acrylic or methacrylic. The term "styrenic" indicates a copolymer polymerized from a monomer or mixture of monomers containing at least one styrene monomer (styrene or substituted styrene) and/or at least one crosslinker, wherein the combined weight of styrene monomers and crosslinkers is at least 50 wt % of the total monomer weight, preferably at least 75 wt %, preferably at least 90 wt %. Styrene monomers include, e.g., styrene, α-methylstyrene, and ethylstyrene. A crosslinker is a monomer containing at least two polymerizable carbon-carbon double bonds, including, e.g., divinyl aromatics; di-, tri- and tetra-(meth)acrylates or (meth)acrylamides; di-, tri- and tetra-allyl ethers and esters; polyallyl and polyvinyl ethers of glycols and polyols. Preferably, the crosslinker(s) has two polymerizable carbon-carbon double bonds, e.g., divinylaromatic crosslinkers, e.g., divinylbenzene. In some embodiments, a styrene polymer is made from a mixture of monomers that is at least 75% styrene and divinylaromatic crosslinkers, more preferably at least 90% styrene and divinylaromatic crosslinkers, and most preferably from a mixture of monomers that consists essentially of styrene and at least one divinylaromatic crosslinker. In other embodiments, a styrene polymer is made from a monomer mixture consisting essentially of at least one divinylaromatic crosslinker. The term "acrylic" indicates a copolymer formed from a mixture of vinyl monomers containing at least one (meth)acrylic acid, ester or amide, along with at least one crosslinker, wherein the combined weight of the (meth)acrylic acid(s), amide(s) or ester(s) and the crosslinker(s) is at least 50 weight percent of the total monomer weight; preferably at least 75%, more preferably at least 90%, and most preferably from a mixture of monomers that consists essentially of at least one (meth) acrylic acid or ester and at least one crosslinker, preferably a difunctional crosslinker, e.g., divinylbenzene. Resins typically are functionalized after polymerization of the component monomers. Resins may comprise more than one functional group.

Preferably, the liquid composition contains from 1 ppm to 100 ppm total of antimicrobial compounds listed above, preferably at least 5 ppm, preferably at least 10 ppm, preferably at least 15 ppm, preferably no more than 75 ppm, preferably no more than 60 ppm, preferably no more than 50 ppm, preferably no more than 40 ppm, preferably no more than 30 ppm. Preferably, the antimicrobial compounds are isothiazolin-3-ones, preferably MIT, CMIT, OIT, DCOIT; BIT and N-alkyl derivatives thereof, especially N-methyl (MBIT) and N-n-butyl (BBIT); and combinations thereof. Preferably, the antimicrobial compounds are selected from MIT, CMIT, BIT, MBIT, BBIT and combinations thereof; preferably MIT, CMIT and combinations thereof. One particular mixture of commercial importance contains MIT and CMIT, preferably in a CMIT:MIT ratio from 4:1 to 1:1, preferably 3.5:1 to 2.5:1, preferably approximately 3:1.

Preferably, the resin is present in an amount from 0.01 to 1 gram of resin per gram of the liquid composition, preferably at least 0.05, preferably at least 0.1, preferably at least 0.13, preferably at least 0.16, preferably no more than 0.75, preferably no more than 0.5, preferably no more than 0.25. Preferably, the liquid composition is a consumer product and the resin is contained in a space within a product container so that the product passes through the resin as it is dispensed. For example, the resin could be trapped between screens or filters in the cap of the product container or in another enclosure above the main product reservoir, i.e., between the main product reservoir and the opening through which product is dispensed. This allows the product to be preserved with antimicrobial compounds, including chlorinated isothiazolin-3-ones, while dispensed product which may contact the product user has greatly reduced levels of antimicrobial compounds. Preferably, the screen or filter has openings with diameters or longest dimensions from 0.05 mm to 0.25 mm, preferably from 0.1 mm to 0.25 mm, preferably from 0.1 mm to 0.22 mm, preferably from 0.1 mm to 0.2 mm. Preferably, the resin is present in an amount from 0.01 to 1 gram of resin per gram of product in the product container, preferably at least 0.05, preferably at least 0.1, preferably at least 0.13, preferably at least 0.16, preferably no more than 0.75, preferably no more than 0.5, preferably no more than 0.25.

The liquid composition treated in the present invention may include, for example: cooling tower water; mineral slurries; wastewater; ballast water; pulp and paper processing fluids; emulsions; dispersions; paints; latices; construction adhesives, such as ceramic adhesives, carpet backing adhesives, and laminating adhesives; industrial or consumer adhesives; photographic chemicals; printing fluids; household products, such as bathroom and kitchen cleaners; personal care products such as cosmetics, toiletries, shampoos, and liquid soaps and detergents; industrial cleaners; floor polishes; laundry rinse water; metalworking fluids; conveyor lubricants; hydraulic fluids; petroleum processing fluids; fuel; oilfield fluids, such as injection water, fracture fluids, and drilling muds; and water from pools and spas. Preferably, the method of the present invention is used to reduce antimicrobial compound levels in personal care products, i.e., those intended to be applied directly to human or animal skin. In personal care compositions, other ingredients may include, e.g., UV radiation-absorbing agents, surfactants, rheology modifiers or thickeners, fragrances, moisturizers, humectants, emollients, conditioning agents, emulsifiers, antistatic aids, pigments, dyes, tints, colorants, antioxidants, reducing agents and oxidizing agents.

Preferably, the liquid composition has a viscosity, measured at 25° C., from 0.001 to 100 Pa·s, preferably from 0.01 to 50 Pa·s, preferably from 1 to 10 Pa·s. Preferably, the pH of the liquid composition, measured at 25° C., is from 3 to 10, preferably from 4.5 to 8, preferably from 5 to 8, preferably from 5.5 to 7.5. Preferably, the liquid composition is contacted with the resin at a temperature from 10° C. to 40° C., preferably from 15° C. to 35° C., preferably from 18° C. to 30° C.

Preferably, the level of crosslinker in the resin is from 0.5% to 20%, preferably from 1% to 12%. Gel resins preferably have a crosslinker level of 0.5% to 4%. Macroporous resins preferably have a crosslinker level of 3% to 14%, preferably from 5% to 12%. In some embodiments the resin is a styrenic resin, typically containing 86% to 99.5% monomer residues of a styrene monomer and 0.5% to 14% residues of a crosslinker. Preferably, the resin is in the form of substantially spherical beads.

Preferably, the resin is a macroporous resin, preferably a macroreticular resin, not a gel-type resin. A macroporous resin is a resin having a surface area from 25 $m^2/g$ to 200 $m^2/g$ and an average pore diameter from 50 Å to 500 Å; preferably a surface area from 30 $m^2/g$ to 80 $m^2/g$ and an average pore diameter from 100 Å to 300 Å. Suitable macroporous resins include, e.g., acrylic resins, styrenic resins, and combinations thereof. Preferably, the harmonic mean particle size of the gel resin is from 100 µm to 2000 µm, preferably from 250 µm to 900 µm, preferably from 300 µm to 750 µm. Calculation of the harmonic mean is well known to those of skill in the art. Preferably, at least 90 volume percent of the resin beads have a particle diameter from 0.9 to 1.1 times the volume average particle diameter. Preferably, the resin has an interpenetrating polymer network. In one embodiment of the invention, the resin comprises functionalized polymerized units of styrene and a crosslinker. Preferably, the crosslinker is diethylenically unsaturated, e.g., divinylbenzene (DVB). Preferably, a functionalized resin has from 1 to 6 meq/g functionality, on a dry basis, preferably at least 2 meq/g, preferably at least 2.5 meq/g, preferably at least 3 meq/g. In some embodiments, the functionalized resin has no more than 5 meq/g functionality, preferably no more than 4 meq/g. Preferably, the resin comprises thiol or thiourea functional groups, preferably thiol groups. The resin may have more than one type of functional group.

Preferably, IPBC is contacted with a cross-linked resin having thiol, thiourea or thioamide functionality, or a weak base anion exchange resin such as a tertiary amine functionalized styrene divinylbenzene resin; preferably thiol or tertiary amine functionality. Preferably, formaldehyde or formaldehyde releasing preservatives are contacted with a cross-linked resin having thiol, thiourea or thioamide functionality, or with silica gel beads covered with polyethyleneimine; preferably a resin having thiol functionality or silica gel beads covered with polyethyleneimine.

Preferably, the resin is confined to form a resin bed, preferably in a container allowing continuous liquid flow through the resin particles. Preferably, the container is a column or reactor. Other resins can be used in combination with the resin(s) having thiol, thiourea or thioamide functionality. Preferably, at least a second resin is used in combination with a first resin having thiol, thiourea or thioamide functionality to control the pH drop typically encountered when an antimicrobial compound, e.g., and isothiazolin-3-one contacts thiol, thiourea or thioamide functional groups in the first resin. Preferably, the second resin is a basic resin, more preferably a weak base ion-exchange resin. Preferably, the second resin has amino functionality, preferably tertiary amino groups. The second resin may be a gel resin or a macroreticular resin. The second resin may be an acrylic resin or a styrenic resin. The first and second resins may be mixed or separated into layers in either order. In one embodiment of the invention, the first resin is the layer encountered first by the liquid composition during treatment of the liquid composition. Preferably, the first resin is at least 50% of the total resin weight, preferably at least 60%, preferably at least 70%, preferably at least 80%, preferably at least 90%. Preferably, the second resin is at least 10% of the total resin weight, preferably at least 20%, preferably at least 30%. Preferably, a resin having antimicrobial activity is used in combination with the first resin to prevent microbial growth in the liquid composition in the resin bed. Resins having antimicrobial activity include, e.g., polylactam powder (U.S. Pat. No. 6,464,887), activated charcoal, anion exchange resins comprising silver ion (U.S. Pat. Nos. 4,076,622 & 7,306,777), polyiodide resin (U.S. Pat. No. 6,680,050) and vitreous antimicrobial agent (U.S. Pat. No. 7,514,093).

EXAMPLES

Example 1

Kinetic Study in Bulk

Resin beads (macroporous styrene copolymer with 3.20 meq/g thiol functionality, 1.1 g/mL wet, 0.5 g dry weight) were dispersed in 50 mL of an aqueous solution of 30 ppm of a 3:1, CMIT:MIT mixture and measurements of residual isothiazolin-3-one concentration were done at several points and the percentage of the original amount remaining was calculated. The results are presented below in Table 1. The pH of the solution changed during the test to a final value of 3-3.5 due to the chemical degradation of isothiazolin-3-ones by the thiol functional groups which produces H+.

TABLE 1

| time, minutes | % residual isothiazolin-3-one |
| --- | --- |
| 0 | 100 |
| 5 | 61.2 |
| 20 | 23.4 |
| 40 | 3.9 |
| 60 | 0.5 |
| 120 | 0.0 |

Example 2

Dynamic Flow Study

A 10 mL syringe was filled with 5 mL or 10 mL of the resin used in Example 1, as indicated below. A 1st flow of 3 mL of a 3:1, CMIT:MIT mixture in water at 22.5 ppm was passed through the resin bed in the syringe. A 2nd flow with identical composition to the first was passed through the same syringe. Isothiazolin-3-one concentrations in the two effluents were measured and the results are presented in Table 2 below.

TABLE 2

| | isothiazolin-3-one amounts in ppm | | |
| --- | --- | --- | --- |
| | initial | $1^{st}$ flow | $2^{nd}$ flow |
| 5 mL resin | MIT = 5.6 | MIT = 0.14 | MIT = 0.45 |
| | CMIT = 16.9 | CMIT = 0.45 | CMIT = 1.26 |
| | total = 22.5 | total = 0.59 | total = 1.71 |
| 10 mL resin | MIT = 5.6 | MIT = nd | MIT = 0.03 |
| | CMIT = 16.9 | CMIT = nd | CMIT = 0.10 |
| | total = 22.5 | total = nd | total = 0.13 | nd = none detected

Example 3

Dynamic Flow Study

The study described in Example 2 was repeated with 10 mL of resin with 15 successive flows of 3 mL each. Results are presented in Table 3 below.

TABLE 3

| eluent amount, mL | isothiazolin-3-one amounts, ppm |
| --- | --- |
| 0 | MIT = 6.28 |
| | CMIT = 18.94 |
| | Total = 25.22 |
| 0-3 | MIT = 0.01 |
| | CMIT = 0.03 |
| | Total = 0.04 |
| 6-9 | MIT = 0.03 |
| | CMIT = 0.08 |
| | Total = 0.11 |
| 12-15 | MIT = 0.02 |
| | CMIT = 0.05 |
| | Total = 0.07 |
| 21-24 | MIT = 0.05 |
| | CMIT = 0.13 |
| | Total = 0.18 |
| 27-30 | MIT = 0.02 |
| | CMIT = 0.05 |
| | Total = 0.07 |
| 42-45 | MIT = 0.10 |
| | CMIT = 0.22 |
| | Total = 0.32 |

Example 4

Flow Study with pH Control

A 10 mL syringe was filled with 10 mL of a combined resin bed 80% of which was the resin used in Example 1 ("R1") and 20% of which was a cross-linked acrylic gel weak base resin (tertiary amine functionality) ("R2"). The syringe was packed with R1 and R2 separately so that biocide solution through the combined resin bed would contact R1 first, followed by R2. Through this resin bed were passed 18 successive flows of 3 mL each of a 3:1, CMIT:MIT mixture in water at 17 ppm. Isothiazolin-3-one concentrations in the effluents and their pH were measured and the results are presented in Table 4 below.

TABLE 4

| eluent amount, mL | ppm isothiazolin-3-one | pH |
|---|---|---|
| 0 | MIT = 4.30<br>CMIT = 12.67 | 6.4 |
| 0-6 | Total = 16.97<br>MIT = 0.23<br>CMIT = 0.47 | 7.4 |
|  | Total = 0.70 |  |
| 24-30 | MIT = 0.26<br>CMIT = 0.53 | 7.3 |
|  | Total = 0.79 |  |
| 48-54 | MIT = 0.29<br>CMIT = 0.58 | 7.3 |
|  | Total = 0.87 |  |

Example 5

Flow Study with pH Control Using Shampoo

Shampoo containing 15 ppm of a 3:1, CMIT:MIT mixture was passed in a downward direction through syringes filled with 10 mL of the resins described in Example 4 in different ratios, as described in the table. Isothiazolin-3-one concentrations in the effluents and their pH were measured and the results are presented in Table 5 below. The shampoo was white due to air bubbles in each case. The viscosity decreased in the second and third tests.

TABLE 5

| eluent amount, mL; and resin proportions | ppm isothiazolin-3-one | pH |
|---|---|---|
| 0 | MIT = 3.75<br>CMIT = 11.31 | 5.9 |
| 6-9;<br>90% R1, 10% R2; | Total = 15.06<br>MIT = 0.34<br>CMIT = 0.92 | 4.1 |
| mixed<br>3-6;<br>80% R1, 20% R2; | Total = 1.26<br>MIT = 0.04<br>CMIT = 0.15 | 3.3 |
| mixed<br>3-6;<br>75% R1, 25% R2; | Total = 0.19<br>MIT = 0.29<br>CMIT = 0.58 | 6.4 |
| R1 on top | Total = 0.87 |  |

Example 6

Kinetic Study in Bulk with Non-Isothiazolone Resins

Resin beads of the indicated types were dispersed in aqueous solutions of the indicated biocides (propylene glycol was added to dissolve IPBC). Resins 1 from example 1 and two additional resins, were tested at a ratio of 2 g resin to 10 mL of biocide solution and measurements of residual biocide concentration were done at several points. Levels of biocides A, B and D were obtained by analysis for total formaldehyde. For biocides B and D the total free formaldehyde results (includes both free formaldehyde and remaining formaldehyde releaser) are calculated back to concentrations of biocide B and D. under conditions that would detect either free formaldehyde or residual biocide A, B or D. The results are presented in the tables below.

| biocide | pH | Control Initial (ppm) | 2-Hr (ppm) | Expected (ppm) |
|---|---|---|---|---|
| A | 6.5 | 494.5 | 477.5 | 514.1 |
| B | 9.13 | 2060.6 | 2135 | 2011.5 |
| C | na | 244.3 | 231.4 | 265 |
| D | 7.06 | 4069.6 | 4542 | 5719 |

| biocide | resin | pH | 5 min. | 30 min. | 2 hr. | 2 hr. % remaining |
|---|---|---|---|---|---|---|
| A | 1 | 4.12 | 158 | 31.7 | 8.9 | 1.8 |
| B |  | 3.91 | 967.5 | 816.2 | 300.8 | 14.6 |
| C |  | na | 11.45 | 0 | 0 | 0 |
| D |  | 3.33 | 2448 | 1874 | 1988 | 48.8 |
| A | 3 | 9.08 | 410.9 | 402.1 | 404.3 | 81.8 |
| B |  | 9.87 | 1880 | 1830.8 | 1827 | 88.7 |
| C |  | na | 10.7 | 0 | 0 | 0 |
| D |  | 7.5 | 3431 | 4035 | 4195 | 103.1 |
| A | 4 | 7.77 | 321.3 | 217.8 | 170 | 34.4 |
| B |  | 7.84 | 1279 | 514 | 274 | 13.3 |
| C |  | na | 194.2 | 199.7 | 197.2 | 80.7 |
| D |  | 7.37 | 2890 | 2219 | 2809 | 69.0 |

Biocide A is formaldehyde;
biocide B is 1-(3-chloroallyl)-3,5,7-triaza-azoniaadamantane;
biocide C is 3-iodopropynylbutylcarbamate (IPBC);
biocide D is 1,3-bis(hydroxymethyl)-5,5-dimethyl-2,4-dioxoimidazolidine.
Biocides B and D are formaldehyde releasers.
Resin 1 is a macroporous styrene copolymer with 3.20 meq/g thiol functionality;
resin 3 is a weak base anion exchange resin (a tertiary amine functionalized styrene divinylbenzene resin);
resin 4 is polyethyleneimine functionalized silica gel beads (ALDRICH #24674-3).

The invention claimed is:

1. A method for reducing antimicrobial compounds in a liquid composition containing at least one antimicrobial compound selected from the group consisting of: isothiazolin-3-ones; 2,2-dibromo-3-nitrilopropionamide; 2-bromo-2-nitropropanediol; dithio-2,2'-bis(benzmethylamide); hexetidine; chlorphenesin and $C_1$-$C_4$ alkyl-4-hydroxybenzoates; said method comprising contacting said liquid composition with a cross-linked resin comprising thiol, thiourea or thioamide functional groups in which the liquid composition is a personal care product.

2. The method of claim 1 in which a weight ratio of the resin to the liquid composition is from 0.01:1 to 1:1.

3. The method of claim 2 in which the antimicrobial compound level in the liquid composition is from 1 ppm to 100 ppm.

4. The method of claim 3 in which the resin comprises thiol functional groups.

5. The method of claim 4 in which the weight ratio of the resin to the liquid composition is from 0.05:1 to 0.5:1 and the resin is a macroporous styrenic resin having a crosslinker level from 3.5% to 14%.

6. The method of claim 5 in which the resin is contained in a space within a product container so that said personal care product passes through the resin as it is dispensed.

7. The method of claim 6 in which said personal care product contains from 5 ppm to 50 ppm total of isothiazolin-3-ones.

8. The method of claim 7 further comprising at least a second resin; wherein said second resin is a basic resin.

9. The method of claim 1 in which the personal care product is selected from the group consisting of cosmetics, toiletries, shampoos, and liquid soaps and detergents.

10. A method for reducing levels of 3-iodopropynylbutylcarbamate in a liquid composition; said method comprising contacting said liquid composition with a cross-linked resin comprising thiol, thiourea, thioamide or amino functional groups in which the liquid composition is a personal care product.

11. The method of claim 10 in which the personal care product is selected from the group consisting of cosmetics, toiletries, shampoos, and liquid soaps and detergents.

12. A method for reducing levels of formaldehyde or formaldehyde-releasing compounds in a liquid composition; said method comprising contacting said liquid composition with a cross-linked resin comprising thiol, thiourea, thioamide or amino functional groups in which the liquid composition is a personal care product.

13. The method of claim 12 in which the personal care product is selected from the group consisting of cosmetics, toiletries, shampoos, and liquid soaps and detergents.

* * * * *